(12) United States Patent
Saito et al.

(10) Patent No.: US 8,323,301 B2
(45) Date of Patent: Dec. 4, 2012

(54) MEDICAL KNIFE

(75) Inventors: Masahiko Saito, Tochigi-ken (JP);
Kanji Matsutani, Tochigi-ken (JP);
Takashi Ina, Tochigi-ken (JP);
Takayuki Matsumoto, Tochigi-ken (JP)

(73) Assignee: Mani Inc., Tochigi-ken (JP)

( * ) Notice: Subject to any disclaimer, the term of this patent is extended or adjusted under 35 U.S.C. 154(b) by 1437 days.

(21) Appl. No.: 10/875,585

(22) Filed: Jun. 25, 2004

(65) Prior Publication Data
US 2005/0004588 A1    Jan. 6, 2005

(30) Foreign Application Priority Data
Jul. 1, 2003    (JP) .................................. 2003-189410

(51) Int. Cl.
*A61B 17/32* (2006.01)
(52) U.S. Cl. ......................................... 606/167; 30/353
(58) Field of Classification Search .................. 606/161, 606/166, 167, 170, 171, 174; 30/353
See application file for complete search history.

(56) References Cited

U.S. PATENT DOCUMENTS

| 5,217,476 | A  | * | 6/1993  | Wishinsky ..................... 606/167 |
| 5,258,002 | A  |   | 11/1993 | Jeffers et al. |
| 5,713,915 | A  | * | 2/1998  | Van Heugten et al. ....... 606/167 |
| 6,547,802 | B1 | * | 4/2003  | Nallakrishnan et al. ...... 606/166 |
| 2002/0026205 | A1 |   | 2/2002  | Matsutani et al. |
| 2003/0004527 | A1 | * | 1/2003  | Matsutani et al. ............ 606/167 |

OTHER PUBLICATIONS

Patent Abstracts of Japan, vol. 20000, No. 26, Jul. 1, 2002 & JP 2001 238890 A, Sep. 4, 2001 & Abstract.

* cited by examiner

*Primary Examiner* — Victor Nguyen
(74) *Attorney, Agent, or Firm* — Smith Patent Ofice

(57) ABSTRACT

A medical knife of the invention having a cutting edge formed along the outer periphery of a blade portion includes a shank; and a blade portion formed continuously from the shank, the blade portion includes a tip portion including a tip whose projected plane shape is formed at an extreme end portion; a maximum width portion having a largest width: a side surface portion formed between the tip portion and the maximum width portion; a cutting edge; a first slanting surface formed along the cutting edge; and a second slanting surface formed along the first slanting surface, wherein the first slanting surface constituting the tip portion has a width larger than that of the first slanting surface constituting the side surface.

2 Claims, 7 Drawing Sheets

(a)

(b)

MEDICAL KNIFE

BACKGROUND OF THE INVENTION

1. Field of the Invention

The present invention relates to a medical knife having a sharp tip, and more specifically, to a medical knife whose durability is enhanced when it pierces tissue.

2. Description of the Related Art

A medical knife is ordinarily used in, for example, an ophthalmic surgery, to form an incision wound to an eyeball. There have been provided various types of medical knives. Among them, there is a medical knife which has a sharp tip at the extreme end thereof, is formed in an approximately rhombic shape using the tip as its apex, and has a cutting edge formed up to the widest portion of the rhombic shape.

As an example of the medical knives, there is a medical knife having a cutting edge formed using a sharp tip formed at the extreme end of a blade portion as its apex. The knife has a first slanting surface, which slants from the cutting edge inwardly upwardly of the blade portion in the thickness direction of the knife on a boundary as a surface including the cutting edge, a second slanting surface formed continuously to the first slanting surface, and an uppermost flat surface formed as an upper surface. Further, the knife has a lower side slanting surface, which slants from the cutting edge inwardly of the blade portion in the thickness direction of the knife, and a flat surface formed continuously to the lower side slanting surface under the above boundary (refer to, for example, Japanese Patent Application Laid-Open No. 2001-238890).

The medical knife has an approximately rhombic planar shape, and the cutting edge is formed up to the widest portion of the rhombic shape. That is, the medical knife is formed in the rhombic shape having the widest portion necessary to form a target incision wound, and the cutting edge is formed along the sides of the knife between the tip and the widest portion.

Further, as shown in FIG. 6, there is also provided a medical knife 51 having no second slanting surface. In the medical knife 51, a tip portion 55 having a sharp tip 54 is formed by causing first slanting surfaces 53 each composed of a flat surface and formed on both the sides of a blade portion 52 to be in coincidence with each other at the tip portion 55.

In the medical knife, which is disclosed in Japanese Patent Application Laid-Open No. 2001-238890, and the medical knife 51, the first and lower side slanting surfaces are formed as surfaces constituting cutting edges to dissect tissue and smoothly finished surfaces to reduce a resistance when tissue is dissected by the knives. The first slanting surface is formed by grinding such that it has an approximately constant width on the side from an extreme end to the widest portion.

In the respective medical knives arranged as described above, a piercing resistance is small when they pierce living body tissue as well as a resistance is also small when they dissect living body tissue. Accordingly, they can accurately dissect an affected area.

Although the medical knives, which have the sharp tip and the cutting edge formed in two directions from the tip to the widest portion, are advantageous in that they have the small piercing resistance when they pierce living body tissue, the medical knives are disadvantageous in that when they pierce living body tissue several times, the piercing resistance of them is increased, that is, they are poor in so-called durability. That is, since the blade portion of the medical knife has a very fine tip of about 1 (m, the tip is bent very easily. For example, even if the tip of the medical knife is slightly in touch with a cloth used in an operation, a finger, and the like before it pierces living body tissue, the cutting quality of the knife is deteriorated.

Further, when the medical knife 51 pierces living body tissue, in particular, the sclera, a hardened blood vessel, and the like of an eyeball, a large force acts on the sharp tip 54 through the piercing, and the tip portion 55 including the tip 54 is bent thereby as shown in, for example, FIG. 7, a problem also arises in that when it is intended to pierce living body tissue with the medical knife 51 whose tip portion 55 is bent, the piercing resistance is extremely increased.

SUMMARY OF THE INVENTION

Accordingly, an object of the present invention is to provide a medical knife that can increase the number of piercing while maintaining a small piercing resistance, that is, to provide a medical knife whose durability is enhanced.

When the present inventors executed an experiment of durability using polyester films to solve the above problem, it was found that since the tip portion 55 of the conventional medical knives was excessively sharp, buckling occurred to the tip portion 55 by the resistance in piercing as shown in FIG. 7, and the tip portion 55 is bent by the bucking. Since the piercing resistance was increased by the buckling, the knives were made unusable.

To cope with the above problem, a medical knife according to the present invention having a cutting edge formed along the outer periphery of a cutting blade includes a shank, and a blade portion formed continuously from the shank, the blade portion includes a tip portion including a tip whose projected plane shape is formed at an extreme end portion; a maximum width portion having a largest width; a side surface portion formed between the tip portion and the maximum width portion; a cutting edge; a first slanting surface formed along the cutting edge; and a second slanting surface formed along the first slanting surface, wherein the first slanting surface constituting the tip portion has a width larger than that of the first slanting surface constituting the side surface.

In the medical knife, the tip portion can be formed in a shape which is unlike to cause budding while securing a piercing property by making the width of the tip portion including the tip larger than the width constituting the side surface portion in the width of the fire slanting surface in the projected plan view of the blade portion Accordingly, deterioration of the piercing property, which is caused by buckling resulting from an increase in the number of piercing, can be prevented to thereby improve durability.

In the medical knife, it is preferable that the projected plane shape of the cutting edge formed along the outer periphery of the blade portion has an approximately linear shape in the side surface portion and has a curved shape in the tip portion. Further, it is preferable that the cross-sectional shape of the cutting edge in the tip portion be composed of a first slanting surface, which is curved to swell upward, and a surface intersecting with the first slanting curved surface.

To make the width of the first slanting surface constituting the cutting edge larger in the tip portion than in the side surface portion of the blade portion, the grinding angle of the tip portion must be made larger than that of the side surface portion in place of grinding the first slanting surface at the same angle from the maximum width portion to the tip portion thereof. With the above grinding, the projected plane shape of the cutting edge in the tip portion, which is formed of the first slanting surface, is formed in a curved shape.

Further, since the cross-sectional shape of the cutting edge constituting the tip portion includes the first slanting surface which is curved to swell upward, the increment of thickness of the blade portion, which increases from the cutting edge toward the inside of the blade portion (in the direction of the center axis of the medical knife), is larger in the vicinity of the cutting edge in comparison with a case that the first slanting surface is formed of a flat surface.

As a result, the tip is not arranged as a sharp tip formed by causing two-directional flat surfaces (first slanting surfaces) to be in coincidence with each other, but it is arranged as a point at which curved surfaces are in coincidence with each other three-dimensionally. Accordingly, even if a force acts on the medical knife in the longitudinal direction thereof when it pierces living body tissue, buckling resulting from the force can be prevented.

DESCRIPTION OF THE PREFERRED EMBODIMENT

Figure 2:
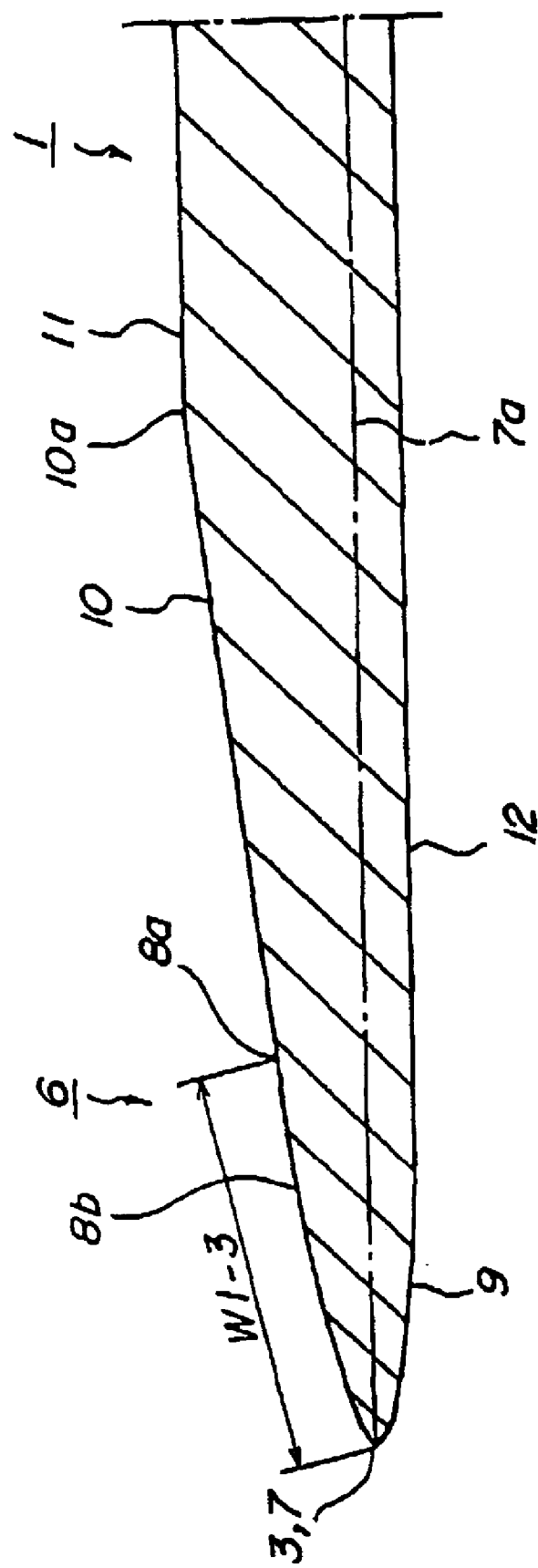
FIG. 2 is a sectional view of the medical knife taken along the line II-II of FIG. 1A.
Figure 3:
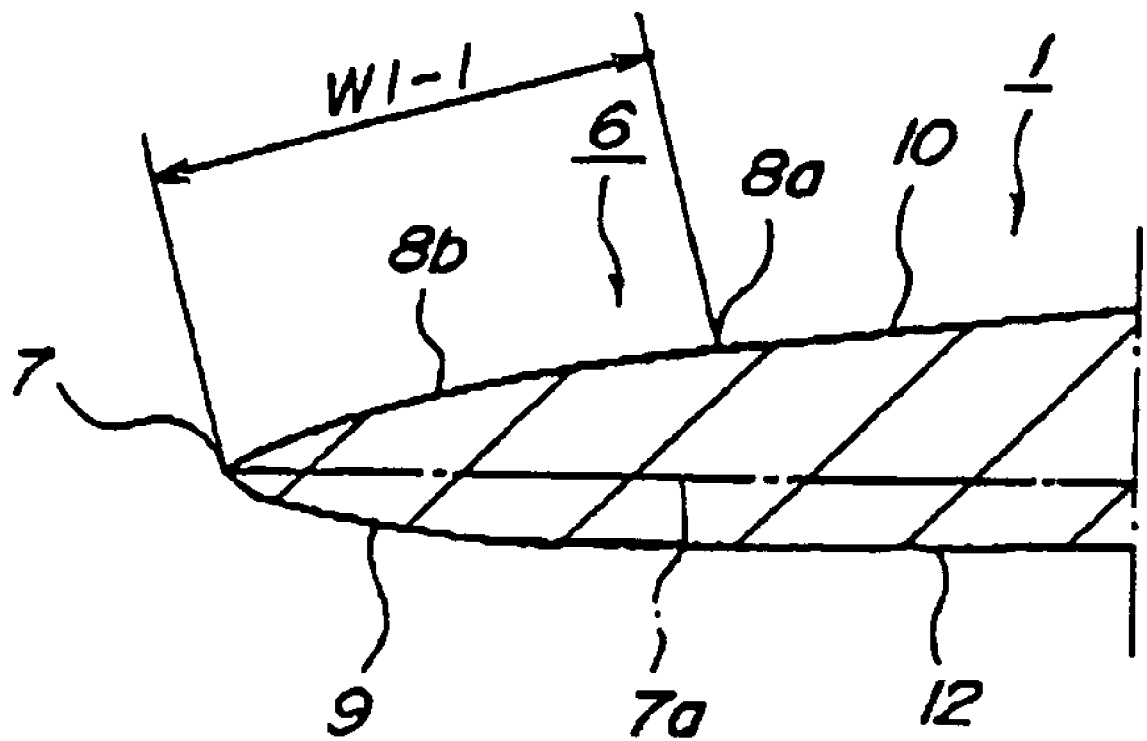
FIG. 3 is a sectional view of the medical knife taken along the line III-III of FIG. 1A.
Figure 4:
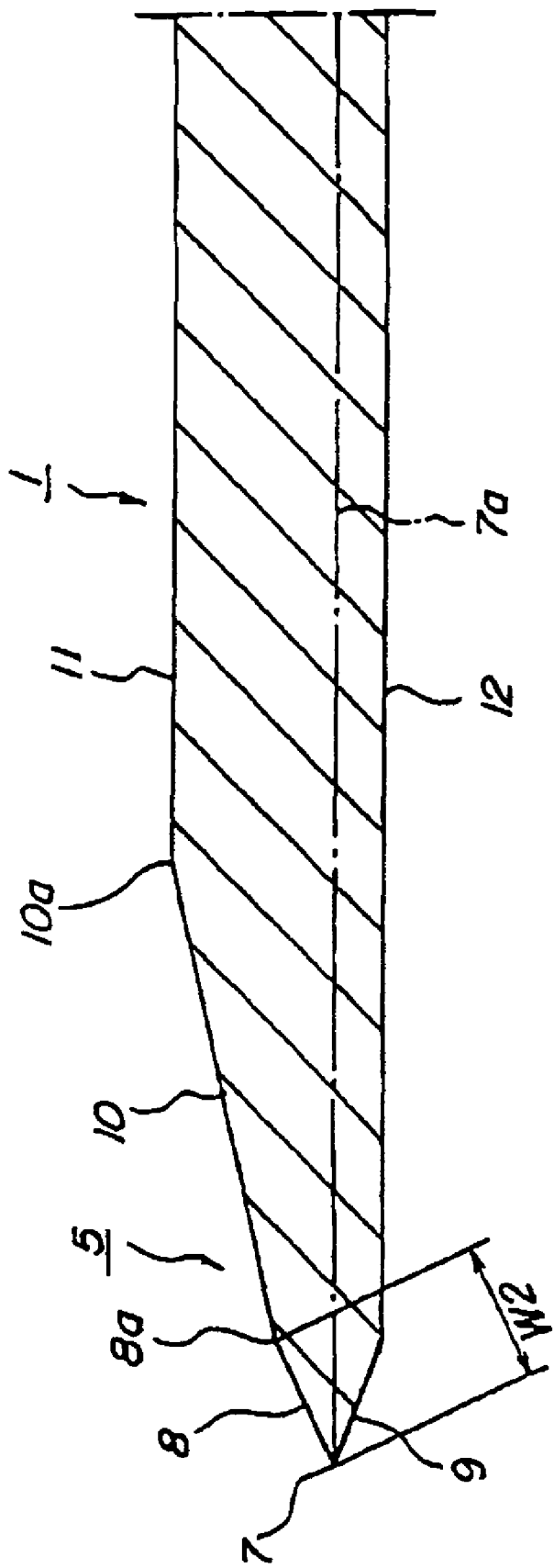
FIG. 4 is a sectional view of the medical knife taken along the line IV-IV of FIG. 1A.
Figure 5:
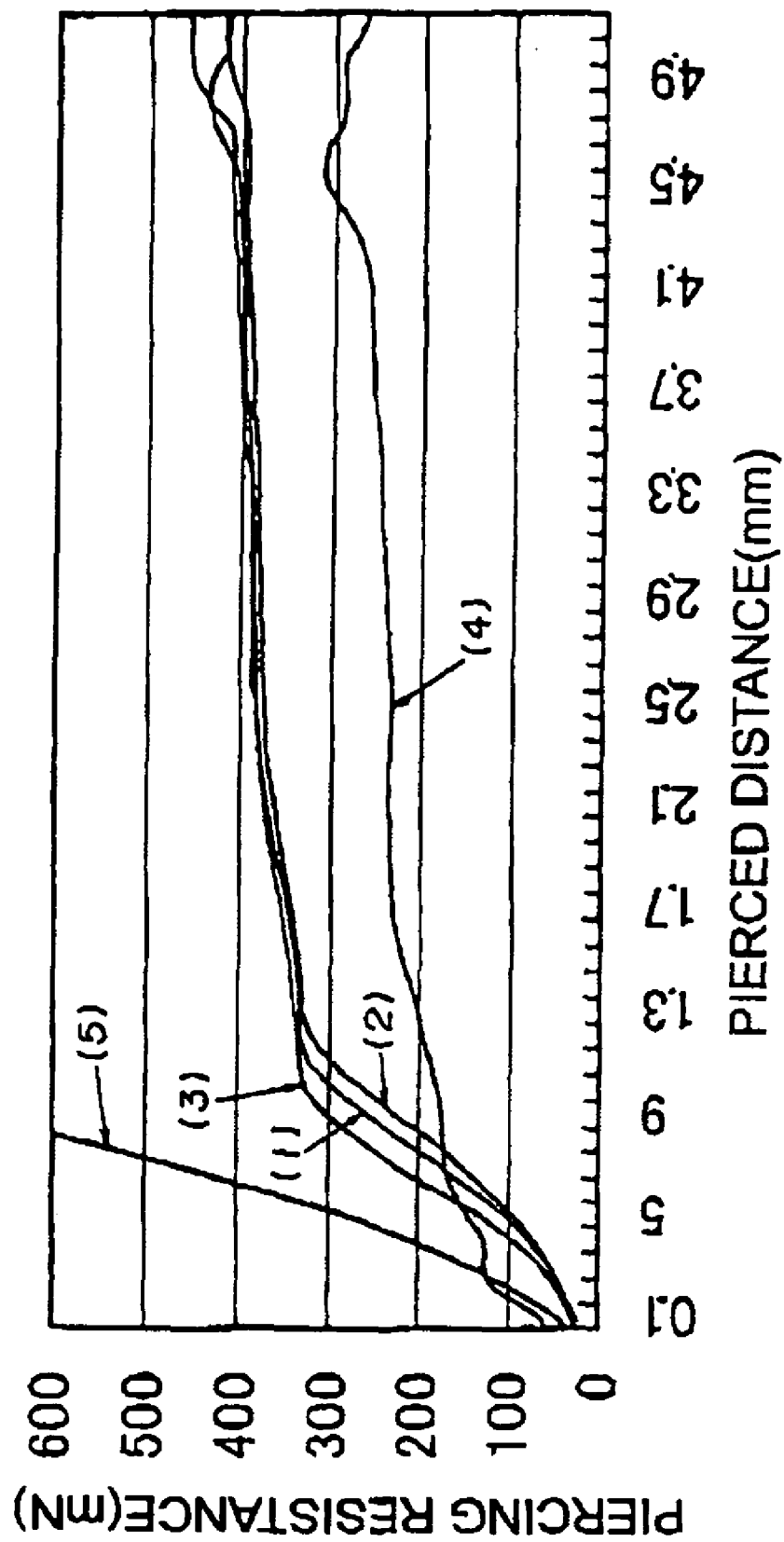
FIG. 5 is a graph showing a result of experiment for comparing the medical knife according to the present invention with a conventional medical knife.

A preferable embodiment of a medical knife (hereinafter, simply referred to as "knife") according to the present invention will be explained below with reference to drawings. FIGS. 1A and 1B are plan views of the knife according to the embodiment. FIG. 2 is a sectional view of the knife taken along the line II-II of FIG. 1A. FIG. 3 is a sectional view of the knife taken along the line III-III of FIG. 1A. FIG. 4 is a sectional view of the knife taken along the line IV-IV of FIG. At FIG. 5 is a graph showing a result of experiment for comparing the knife according to the present invention with a conventional knife.

The knife according to the present invention has a function for piercing an affected area of an eyeball, and the like, forming an initial incision wound, and dissecting living body tissue from the initial incision wound as a start point as well as pressing and broadening the living body tissue, and when an operation for burying a lens in an eyeball is executed, the knife can form an incision wound having a length through which the tip of an ultrasonic emulsifying/suctioning device can be inserted to absorb a crystal lens from the eyeball and an incision wound having a length through which a lens, which is buried into the eyeball, can be inserted. In particular, the durability of the knife is enhanced by increasing the number of times of piercing executed in a state that durability is maintained, that is, in a state that a piercing resistance is small by forming the extreme end of the blade portion of the knife in a special shape.

A material for constituting the knife according to the present invention is not particularly limited, and steels such as stainless steel, carbon steel, and the like can be used. However, when rustproof and easiness in processing is taken into consideration, it is preferable that the material is composed of stainless steel, and in particular, austenitic stainless steel is preferable.

When the austenitic stainless steel is used as the material, it is preferable to extend the structure of the austenitic stainless steel in a fiber state by subjecting it to cold plastic working at a predetermined working ratio to increase the hardness of the material and to subject it to press working, polishing, and other necessary working while maintaining the fiber-state structure.

As shown in FIG. 1A, a knife A is composed of a blade portion 1 and a shank 2 continuous to the blade portion 1, a tip 3 is formed at the extreme end of the blade portion 1, a maximum width portion 4 of the blade portion 1 is formed at a position spaced apart from the tip 3 of the blade portion 1, and a side surface portion 5 is formed between the tip 3 and the maximum width portion 4. Further, a tip portion 6 is formed within a range having a predetermined dimension and including the tip 3. Accordingly, the planar shape of the knife A is formed in an approximately rhombic shape from the blade portion 1 to the shank 2.

The detailed dimensions of the knife A such as the distance from the tip 3 to the maximum width portion 4, the width of the maximum width portion 4, and the like are variously set according to an object of the knife A, for example, according to the specification of an incision wound, for example, the dimension and the like thereof.

A cutting edge 7 is formed along the outer edge of the blade portion 1. The cutting edge 7 has a function for dissecting living body tissue and is formed by causing a first slanting surface 8, which is formed on a boundary acting as a surface 7a including the cut edge 7, to intersect with a lower side slanting surface 9 which is formed under the boundary. Since the first slanting surface 8 and the lower side slanting surface 9 form the cutting edge 7 in cooperation with each other as described above, these slanting surfaces 8 and 9 are formed of a ground surface having a high degree of smoothness.

A second slanting surface 10 is formed along the fist slanting surface 8 formed on the boundary of the blade portion 1, and a boundary line 8a is formed along the boundary between both the slanting surfaces 8 and 10. Since the second slanting surface 10 does not have a function for constituting the edge 7 (as a cutting blade), it is not always necessary to form the second slanting surface of a ground surface having a high degree of smooth and it may be formed of a surface formed by press working or of a rough ground surface. Further, an upper flat surface 11 is formed along the second slanting surface 10 and may be composed of a surface formed by press working or a rough ground surface likewise the second slanting surfaces 10.

A lower side flat surface 12 is formed continuously to the lower side slanting surface 9 formed under the boundary of the blade portion 1. Since the lower side flat surface 12 is formed as a surface which does not have a function for constituting the edge 7 (as a cutting blade), the lower side flat surface 12 is not necessarily a ground surface having a high degree of smoothness and may be composed of a surface formed by press working or a rough ground surface.

Figure 1:
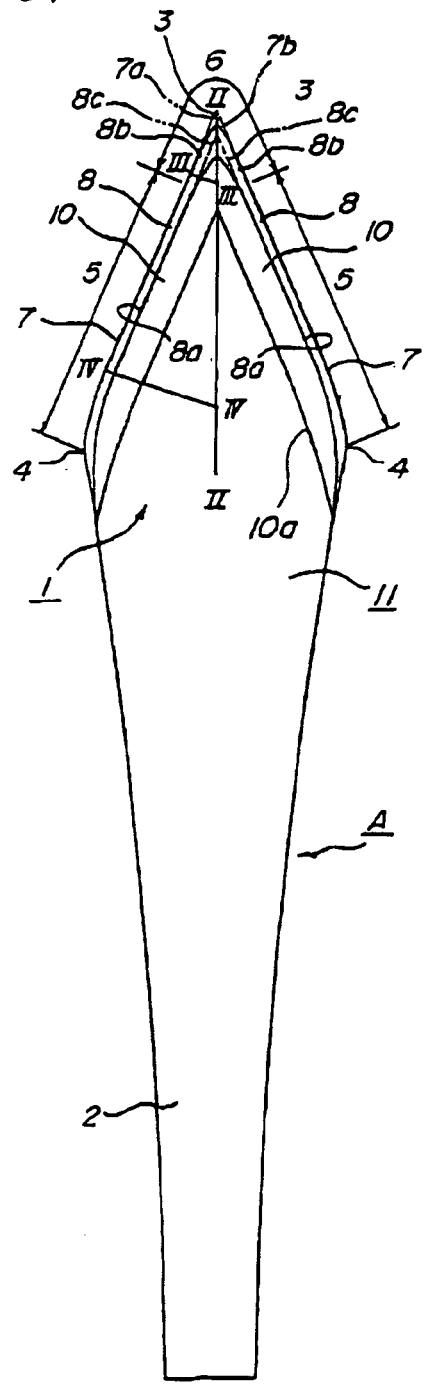
FIGS. 1A and 1B are plan views of a medical knife according to the present embodiment.
Figure 1:
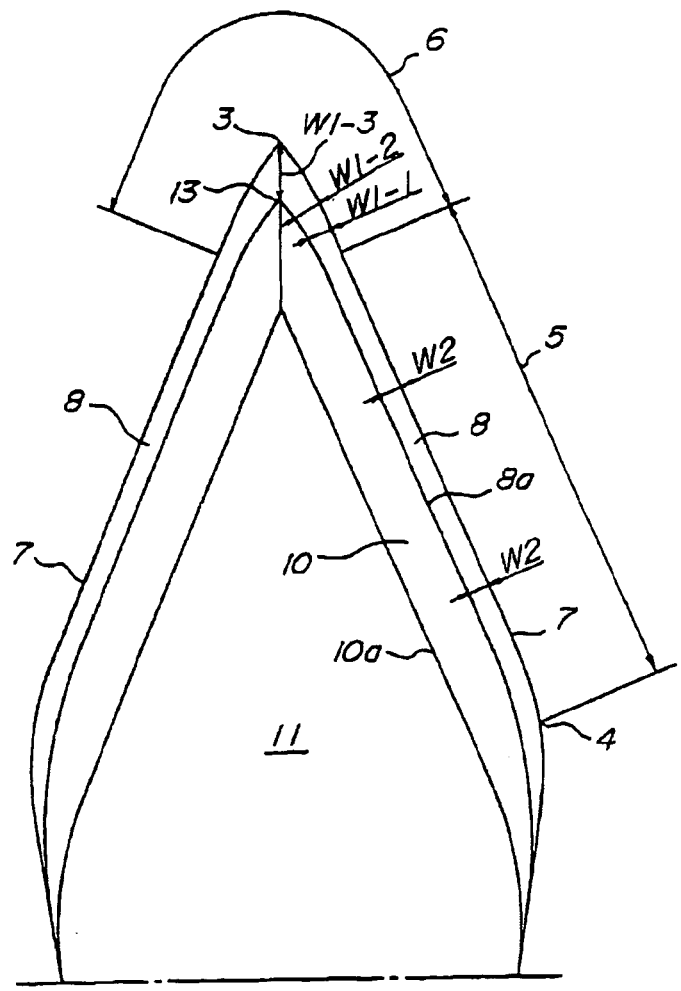

In the side surface portion 5 of the blade portion 1, the first slanting surface 8 is formed of a flat surface as shown in FIG. 4 and has the same width W2 as shown in FIG. 1.

In other words, the range, in which the first slanting surface 8 is formed of the flat surface having the same width W2, corresponds to the side surface portion 5 in the blade portion 1. In the side surface portion 5, the lower side slanting surface 9, which is formed on the lower side of the surface 7a including the cutting edge 7, is also formed of a flat surface. Accordingly, the cutting edge 7 is formed in an acute shape having a sharp tip by causing the two flat surfaces to intersect with each other. In the side surface portion 5 arranged as described above, the boundary line 8a acting as the boundary between the first slanting surface 8 and the second slanting surface 10 is composed of an distinct edge, and further a boundary line 10a is formed between the second slanting surface 10 and the not-worked upper flat surface 11.

The first slanting surface 8 and the lower side slanting surface 9 can be formed using a grinding material having a high degree of flatness and appropriate rigidity. A grinding stone, a belt-shaped grinding stone whose back surface is supported by a frame having high rigidity, and the like are available as the grinding material, and they can be selectively used.

As shown in FIG. 1B, in the tip portion 6 of the blade portion 1, a tip portion first slanting surface 8b (hereinafter, the first slanting surface constituting the tip portion 6 is denoted by 8b) is formed by a gently curved surface as shown in FIGS. 2 and 3, the width W1 of the tip portion first slanting surface 8b is larger than the width W2 of the first slanting surface 8 of the side surface portion 5, and the width W1 of the tip portion first slanting surface 8b gradually increases as it approaches the tip 3 from the vicinity of the side surface portion 5 (W1-3>W1-2>W1-1). Further, at the tip portion 6, the lower side slanting surface 9 formed on a lower portion the surface 7a including the cutting edge 7 is also formed of a gently curved surface. The tangent lines of the curved surfaces, which constitute the first slanting surface Sb and the lower side slanting surface 9, have an acute angle with respect to the surface 7a including the cutting edge 7. More specifically, since the curved surface of the first slanting surface 8b and the curved surface of the lower side slanting surface 9 are formed individually, the intersecting portion (cutting edge 7) of both the slanting surfaces is formed as a discontinuous line. Note that the widths W1-1, W1-2, W1-3, and W2 of the first slating surface 8 are orthogonal to the cutting edge 7 and have the lengths of line segments up to the boundary line 8a between the first slanting surface 8 and the second slanting surface 10. Further, when a line orthogonal to the cutting edge 7 does not intersect with the boundary line 8a in the first slanting surface 8b at the tip portion 6, the line segment is composed of a line segment up to the extreme end 13 of the boundary line 8a.

Accordingly, the cutting edge 7 is arranged so as to be sharp at its extreme end by causing the two curved surfaces, which are formed on and under the surface 7a including the cutting edge 7, to intersect with each other. However, the wall thickness of the knife A in the portion thereof, which is located in the vicinity of the cutting edge 7 inwardly of the knife A (in the directions toward the upper flat surface 11 and the lower side flat surface 12) is formed larger than that of the cutting edge 7 on the side surface portion 5. More specifically, the increment of thickness of the first slanting surface 8b and the lower slanting surface 9 with respect to any position of the knife A, which is spaced apart from the cutting edge 7 that acts as a start point to the inside of the knife A, is larger than that of the first slanting surface 8 and the lower side slanting surface 9 on the side surface portion 5, thereby the anti-buckling performance of the knife A can be enhanced. Any internal portion of the knife A which is continuous to the above position (that is, any portion located more inwardly of the knife A than any portion in the vicinity of the cut edge 7) has a slanting angle more gentle than that of the cutting edge 7 on the side surface portion 5 (has an acute angle).

Accordingly, the cutting edge 7 maintains an acute angle at the tip portion 6 when it is viewed in a broad perspective, thereby the piercing resistance of the knife A can be reduced, and further the durability thereof can be enhanced because the anti-buckling performance is enhanced.

The cutting edge 7, which is formed by the first slanting surface 8b and the lower side slanting surface 9 as described above, draws a gentle curve from the boundary of it to the side surface portion 5 or from the vicinity of the boundary toward the tip 3 when it is viewed on plane (it is viewed from a direction orthogonal to the surface 7a including the cutting edge 7, which will be applied to the following description likewise). For example, the first slanting surface 8b, which is formed on the upper side of the surface 7a including the cutting edge 7, will be explained.

The interval between the two-dot-and-dash line 7b extending from the cutting edge 7 and the two-dot-and-dash line 8c extending from the boundary line 8a has the same width as that of the first slanting surface 8 which constitutes the side surface portion 5 and is formed of a flat surface. When the first slanting surface 8 formed of the flat surface as described above is formed to the first slanting surface 8b which is curved to swell upward, the flat surface is ground on both the end sides thereof (on the sides of the extending lines 7b and 8b), thereby the portions of the knife A shown by the extending lines 7b and 8b are ground and backed off. The width of the first slanting surface 8b constituting the tip portion 6 is made lager than that of the first slanting surface 8 constituting the side surface portion 5 by forming the first slanting surface 8b of the tip portion 6 as described above.

Then, the shape of the cutting edge 7 viewed in plane can be curved at the tip portion 6 by forming the first slanting surface 8b so that it is backed off to the inside of the knife A from the side surface portion 5 to the tip 3.

In this case, the curvature of the first slanting surface 8b gradually changes from the boundary between it and the side outface portion 5 toward the tip 3.

Further, the cutting edge 7 is formed at the tip portion 6 by the intersection of the curved surface of the first slanting surface 8b with that of the lower side slanting surface 9. Accordingly, in the vicinity of the cutting edge 7, the increment of thickness at any position slightly spaced apart therefrom to the inside of the knife A (in the directions toward the upper flat surface 11 and the lower side flat surface 12) is larger than the increment of thickness of the cutting edge 7 on the side surface portion 5, thereby a resistance against buckling is increased.

The shape of the curved surfaces of the first slanting surface 8b and the lower side slanting surface 9, which constitute the tip portion 6 arranged as described above, is not particularly restricted. That is, the property of the curved surfaces constituting the respective slanting surfaces 8b and 9 of such as the partial curvature and the like is not restricted. The first slanting surface 8b and the lower side slanting surface 9 can be formed using grinding stones on which curved grinding surfaces are previously formed.

The tip 3 is formed by causing the first slanting surface 8b and the lower side slanting surface 9 each having the curved surface as described above to be in coincidence with each other from two directions viewed in plane and as well as by causing them to be in coincidence with each other from upper and lower sides of the surface 7a including the cutting edge 7 (in the thickness direction of the knife A). More specifically, the tip 3 is formed by causing the first slanting surface 8b, which is formed on the up portion of the surface 7a and curved in two the directions, to be in coincidence with the lower side slanting surface 9, which is formed on the lower portion of the surface 7a and curved in the two directions.

Accordingly, although the tip 3 is formed of a sharp point, the increment of thickness in the vicinity of the point is larger than that of a tip formed of a flat surface. More specifically, the tip 3 is formed by causing the first slanting surface 8b curved in the two directions to intersect with the lower side slanting surface 9 curved in the two directions at the one point Accordingly, in the vicinity of the tip 3, the increment of thickness of the tip 3 at any position slightly spaced apart from the tip 3 in the axial direction (longitudinal direction) of the knife A is larger than the increment of thickness of the cutting edge 7 on the side surface portion 5. In other words, although the tip 3 is formed of the sharp point, the thickness of the tip 3 is abruptly increased at any position even if it is slightly spaced apart from the sharp point. Further, any internal portion of the knife A, which is continuous to the tip 3 (that is, any portion located more inwardly of the knife A than any portion in the vicinity of the cutting edge 7) has a slanting angle more gentle than that of the cutting edge 7 on the side surface portion 5 (has an acute angle).

Accordingly, when the tip 3 pierces living body tissue passing through it, it is possible to realize a smooth dissection because with an initial piercing resistance is small. Further, a resistance against bucking is increased in comparison with a conventional knife arranged by causing slanting surfaces, which are flat in four directions, to be in coincidence with each other. Accordingly, even if the tip 3 pierces the living body tissue repeatedly, buckling of the tip portion 6 including the tip 3 can be prevented, thereby the durability of the tip 3 can be improved.

Figure 6:
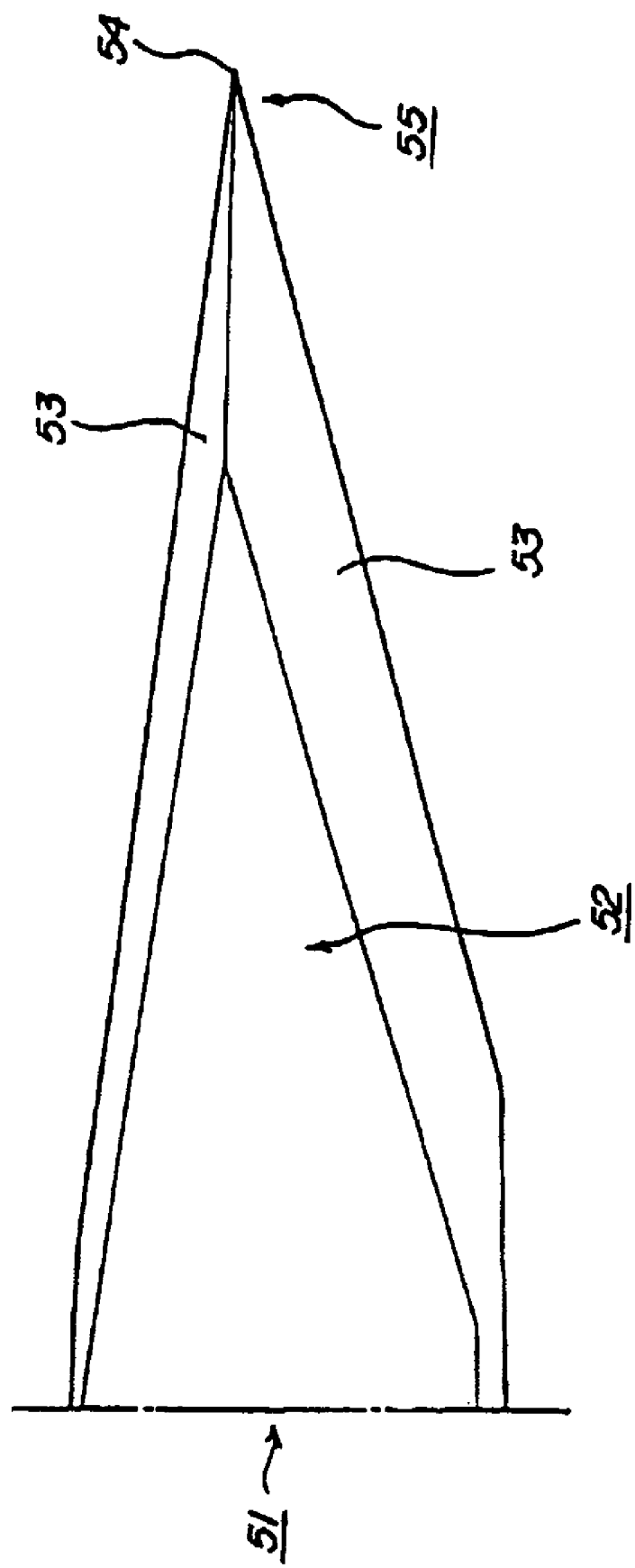
FIG. 6 is a perspective view of the conventional medical knife.

The present inventors executed an experiment for comparing the durability of the knife A arranged as described above with that of the conventional medical knife 51 shown in FIG. 6. In the experiment, the knife A and the conventional medical knife 51 were set on a load cell vertically downwardly, films (38 (m thick polyester films) were disposed below the knives and pierced by lowering the knife A and the conventional knife at a predetermined speed, and the relation between a pierced distance and a piercing resistance was measured as to each of the knives. This experiment method is often used to examine the cutting quality of medical knives, suture needles, and the like because a result of experiment has a very small amount of dispersion because no living body tissue is used. It has been confirmed that when the cutting quality of a knife is bad in the experiment, the cutting quality of it is also bad when it is used in a living body tissue.

FIG. 5 shows a result of the experiment. Note that in the figure, a line (1) shows the piercing resistance of the knife A according to the present embodiment at a first time, a line (2) shows the piercing resistance of the knife A at a sixth time, and a line (3) shows the piercing resistance of the knife A at a twelfth time. Further, a line (4) show the piercing resistance of the conventional medical knife at a first time, and a line (5) shows the piercing resistance of the conventional medical knife at second time.

Figure 7:
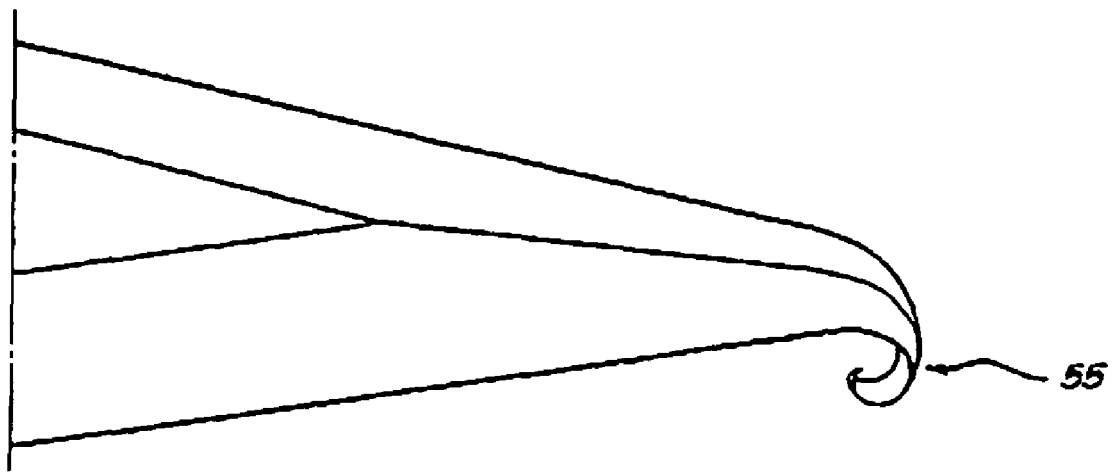
FIG. 7 is a view explaining a problem of the conventional medical knife.

As a result of the experiment, the piercing resistance of the conventional medical knife obtained in the experiment executed at the first time has the smallest experiment value of all the experiment values as shown by the line (4), and the piercing resistance of it obtained in the experiment executed at the second time has the largest experiment value of all the experiment values as shown by the line (5). That is, since the tip of the conventional medical knife is formed very sharply (refer to FIG. 6), it has a small piercing resistance to tissue and thus can exhibit very excellent cutting quality. However, at the second time, the tip portion of the knife is bent due to buckling (refer to FIG. 7) and the piercing resistance thereof is extremely increased. In this experiment, the conventional medical knife could not pierce the film at the second time.

In contrast, the knife A according to the embodiment exhibits approximately the same tendency from the first to twelfth times as shown by the lines (1) to (3). That is, although the piercing resistance of the knife A is larger than that of the conventional medical knife at the first time, it has approximate the same piercing resistance regardless of an increase in the number of piercing and can exhibit a stable piercing property.

In particular, since the knife A can obtain approximately the same piercing resistance as that of the first time even at the twelfth time, the knife A can endure the repeated use thereof, and thus it can be said that the durability of the knife A is enhanced. It is deemed that since the tip 3 is formed by causing the four curved surfaces to be in coincidence with the each other, the tip 3 can resist a force acting on it vertically (force acting along the longitudinal direction of the blade portion 1 from the tip 3) to thereby greatly reduce a possibility for causing buckling although the tip 3 itself is duller than that of the conventional medical knife and its piercing resistance is increased accordingly.

As described above in detail, in the knife according to the present invention, the thickness of the blade portion for forming the tip can be increased while maintaining the sharpness of the tip by making the width of the first slanting surface, which constitutes the tip portion including the sharp tip formed at the extreme end of the blade portion, larger than that of the first slanting surface which constitutes the side surface portion. Accordingly, the tip can endure the force acting thereon when tissue is pierced thereby. As a result, the durability of the tip can sufficiently enhanced against a force acting thereon repeatedly.

What is claimed is:

1. A medical knife having a cutting edge formed along the outer periphery of a blade portion comprising:
   (a) a shank; and
   (b) a blade portion formed contiguously with the shank, the blade portion comprising:
      (i) a tip portion including a tip whose projected plane shape is formed at an extreme end of the blade portion;
      (ii) a maximum width portion having a largest width;
      (iii) a side surface portion formed between the tip portion and the maximum width portion;
      (iv) a cutting edge defining an outer periphery of the blade portion;
      (v) a first slanting surface formed along the cutting edge; and
      (vi) a second slanting surface formed inside the first slanting surface and formed along the first slanting surface,
   wherein the first slanting surface constituting the tip portion has a width larger than that of the first slanting surface constituting the side surface portion; wherein a sectional shape of the cutting edge in the tip portion of the blade portion is formed of a first curved slanting surface swelled upward and a surface intersecting the first slanting curved surface.

2. A medical knife according to claim 1, wherein a projected plane shape of the cutting edge defining the outer periphery of the blade portion has an approximately linear shape on the side surface portion and has a curved shape at the tip portion.

* * * * *